United States Patent [19]
Williams et al.

[11] Patent Number: 4,782,647
[45] Date of Patent: Nov. 8, 1988

[54] FLEXIBLE PACKAGING AND THE METHOD OF PRODUCTION

[75] Inventors: Joel L. Williams, Cary, N.C.; Walter P. Miller, III, Parsippany, N.J.

[73] Assignee: Becton, Dickinson and Company, Franklin Lakes, N.J.

[21] Appl. No.: 109,679

[22] Filed: Oct. 8, 1987

[51] Int. Cl.$^4$ .................... B65B 47/02; B65B 61/00
[52] U.S. Cl. ........................ 53/454; 53/141; 53/560
[58] Field of Search ............... 53/454, 433, 453, 141, 53/559, 560, 511, 546, 375; 206/439

[56] References Cited

U.S. PATENT DOCUMENTS

| | | | |
|---|---|---|---|
| 2,497,212 | 2/1950 | Donofrio | 53/141 X |
| 3,418,140 | 12/1968 | Fisher | 53/453 X |
| 3,805,486 | 4/1974 | Mahaffy et al. | 53/559 |
| 4,034,536 | 7/1977 | Mahaffy et al. | 53/453 X |
| 4,265,070 | 5/1981 | Mainberger et al. | 53/559 X |
| 4,306,656 | 12/1981 | Dahlem | 206/439 X |
| 4,365,456 | 12/1982 | Ullman | 53/375 X |
| 4,452,679 | 6/1984 | Dunn et al. | |
| 4,614,076 | 9/1986 | Rathemacher | 53/433 |
| 4,655,767 | 4/1987 | Woodard et al. | |

OTHER PUBLICATIONS

"The Corona Discharge, Its Properties and Specific Uses", *Pure & Appl. Chem.*, vol. 57, No. 9, pp. 1353-1362, 1985.

"Work in Progress on Corona Discharge Treatment", *Int. J. Adhesion and Adhesives*, Oct. 1984, pp. 184-185.

"Effects of Corona-Discharge-Induced Oxygen Ion Beams and Electric Fields on Silicon Oxidation Kinetics", *Journal of the Electrochemical Society*, vol. 132(7), Jul. 1985, pp. 1659-1663.

*Primary Examiner*—Horace M. Culver
*Attorney, Agent, or Firm*—Robert P. Grindle

[57] ABSTRACT

Methods are provided for producing flexible packages and particularly transdermal medication patches. The method includes the continuous and rapid production of a plurality of such packages while continuously treating one portion of the laminate forming the package by corona discharge in order to modify the surface adhesion properties thereof to provide, simultaneously, a proper seal of a transdermal membrane in the laminate forming the package, while maintaining the desired medication dispensing properties thereof.

4 Claims, 2 Drawing Sheets

FLEXIBLE PACKAGING AND THE METHOD OF PRODUCTION

BACKGROUND AND STATEMENT OF THE INVENTION

The invention described and claimed herein is related to U.S. Application Ser. No. 737,306 filed May 23, 1985, now U.S. Pat. No. 4,614,076, issued Sept. 30, 1986 which is incorporated herein by reference in its entirety. This invention relates to methods and apparatus for the production of flexible packaging wherein each individual package contains a sealed controlled quantity of a non-solid substance. Representative of such substances are ointments, gels and salves, for example, More particularly, this invention relates to the continuous surface treatment of at least one web forming the flexible packaging so as to modify the surface thereof to enhance the sealing properties in the formation of the packages of the invention. In this connection, the approach may include intermittent or continuous formation of the packages.

In flexible packaging of the kind to which this invention relates it is important that a precise controlled quantity of material be contained in each individual package if, for example, the ointment, gel or salve is a medication requiring a precise quantity for later medical application to a patient. Such applications include, for example, transdermal medication in which a flexible package includes a special membrane with an adhesive surface, or a surface with a peripheral adhesive border, which may be applied to the skin of a patient for a controlled administration of a medication over a period of time. Such flexible packages include a peel-off film over the adhesive surface, which the user peels off immediately prior to applying the package to his skin.

With the invention herein, methods and apparatus are provided for the continuous or intermittent and rapid production of a plurality of such flexible packaging containing a non-solid material by joining the two webs together in the nip of sealing rolls or platen dies, depending upon which form of packaging machinery is being utilized. This is achieved specifically with the invention here with two dissimilar materials. Ordinarily, such materials will not provide a proper seal. It is within the purview of this invention to provide such continuous packaging using dissimilar thermoplastic by exposing one web to be joined subsequently in a heated nip with a corona discharge so as to modify the surface chemistry thereof to adhere in proper sealing relationship to the opposing web.

That is, a plurality of such packages may be formed simultaneously across the width of the webs being joined together in the roller nip in one form of packaging of a pair of rollers which cooperate to provide, automatically and simultaneously, for the formation, and sealing of each individual flexible package in the webs. Alternatively, opposed platens may form the packages by cooperative operation with each other. By utilizing the continuous corona exposure, a backing web of a single thermoplastic material may be used rather than a laminate including a separate material for adherence to the opposing web, or bonding agents, both expensive propositions.

Thus, flexible packages may be produced on a continuous basis in a much more simplified and economical manner. The invention contemplates the use of cooperating sealing rollers in which one roll includes pockets for forming the individual flexible packages cooperating with a second roll which provides a proper pressure at the nip of the rolls in order to form the individual packages across the width of the webs being joined. As will be understood by practitioners of the packaging art opposed platens may be used, also, wherein one includes pockets and the other provides flat plate pressure.

Transdermal membranes utilized for packages of the kind discussed herein have properties specifically selected to produce the desired passage of medication, once the package is opened, and the membrane adhered to the skin. However, the properties which provide this desired, controlled passage of medication are adverse to sealing properties required in the laminated package as produced and prior to use. The invention here provides a chemical surface modification so as to provide simultaneously the desired sealing and medication passage properties.

Thus, the webs contain thermoplastic resin materials which may be joined and sealed under the application of heat and pressure. In one representative form of machinery to be described below, crimp rolls which cooperate to provide the sealed packaging on a continuous basis are heated in order to provide the appropriate sealing of the two webs together during the simultaneous forming, and sealing of the flexible packages. Once the two webs are joined together, the packages may be cut from the web by opposed cooperating rotary die rolls.

Before describing this invention in more detail, it may be well to note that silicone rubber membranes may be used herein for the actual transmission of medication, once a patch is in place on the skin of a patient. Such materials include generally a polydimethyl siloxane copolymer (silicone film), such as LSR 44210 SILASTIC TM a product of Dow Corning Corp., Midland, Mich. Also used experimentally is Dow Experimental #E6669-39 silicone sheeting. The backing material, which forms the opposite side of the patch and provides "body" therefor may be, for example, a polyester film laminated to a ethylene acrylic acid copolymer film. With respect to the silicone membrane mentioned above, the very properties that make it appropriate for dispensing medication in a controlled manner, make the material less desirable for sealing to a backing film. Thus, the invention herein solves that by modifying the surface to make the membrane have two diametrically opposite but desired properties for accommodating a transdermal patch application.

The flexible packaging procedures involved herein apply to a variety of different materials which may be packages, as long as they contain a liquid component. That is, ointments, gels, salves and even oils may be contained within the flexible packaging herein, as long as the material involved will, when dropped on the web and prior to being sealed, hold a momentary selfcontained body until such time as the material is properly joined in the flexible packaging formed by the methods and apparatus herein. It will be understood, furthermore, that a variety of different film materials comprised of thermoplastics may be utilized in the processing of the invention herein for forming the webs which are joined together to produce the flexible packaging. For example, polyvinyl chloride, polyvinylidene chloride, polyesters, polyethylene and polypropylene are all materials which may be utilized.

With the foregoing and additional objects in view, this invention will now be described in more detail, and other objects and advantages thereof will be apparent from the following description, the accompanying drawings, and the appended claims.

As purely illustrative of apparatus which may be used for carrying out the process of this invention, one may note the attached drawings in which a schematic illustration of apparatus for carrying out the invention is shown together with a representative package which may be formed in accordance with this invention.

DETAILED DESCRIPTION OF THE INVENTION

Figure 1:
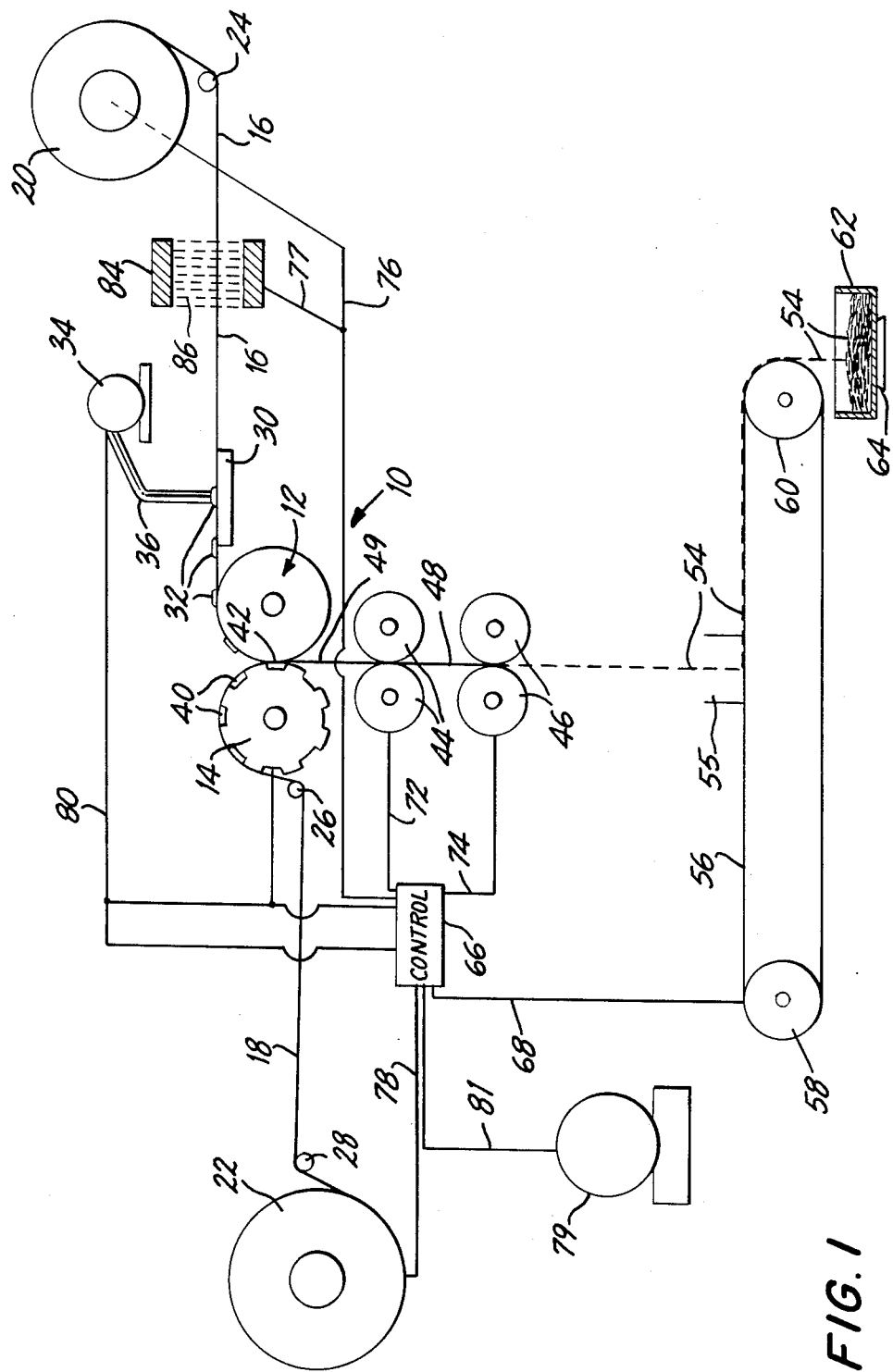
FIG. 1 is a schematic illustration of one form of apparatus which may be used for carrying out this invention.

Referring to the drawings in which like reference characters refer to like parts throughout the several views thereof a roller type apparatus for producing on a non-stepping continuous basis, evacuated flexible packaging containing materials with a liquid component therein is shown generally at 10. Thus, cooperating crimp rolls 12, 14 form from webs 16, 18, a joined web 49 at cooperating nip 42. The web 16 is taken from a supply roll 20 with web 16 passing over a guide roll 24 prior to passing through station 84.

Station 84 is a corona discharge station wherein the surface chemistry of web 16 is modified to improve the adhesion properties thereof to a dissimilar material in the form of web 18. That is, web 16 is heat sealed to web 18 at nip 42. Web 16 may be a laminate, the top surface of which may be, for example, a silicone film, while web 18 may be a polyester laminated to an ethylene acrylic acid copolymer film (EAA), with webs 16, 18 being two dissimilar materials for sealing purposes. By chemically modifying web 16 by the corona 86 at station 84 in air, polar oxidative groups are formed on the surface which will bind with the polar oxidative groups in web 18 during the subsequent heat sealing operation.

Corona discharge is a conventional procedure utilized for modifying polymeric surfaces, for example, to change the chemical characteristics thereof. For more detail concerning corona discharge and the apparatus thereof, attention is claled to the *Journal of the Electrochemical Society*, Vol. 132(7) 1985, "Effects of Corona-Discharge-Induced Oxygen Ion Beams and Electric Fields on Silicon Oxidation Kinetics" by Douglas N. Modlin, which is hereby incorporated by reference in its entirety.

Referring again to FIG. 1, corona treated web 16 passes to station 30 where quantitities 32 of an ointment containing nitroglycerin, for example, to be incorporated into the plurality of packages is deposited on web 16 from an ointment supply 34 which passes through tubes 36 for the deposit of the material 32 on web 16. Although not shown, it will be understood that a plurality of material deposits 32 are deposited simultaneously across the width of web 16. Thereafter, the deposited materials 32 pass to the cooperating nip 42 between rolls 12, 14 wherein the material passes into cooperating spaces 40 on roll 14. The periphery of the pockets or spaces 40 on roll 14 serves as the border for the sealing of the material 32 between the webs 16, 18. Web 18 is drawn from a supply roll 22 and passes over guide rolls 28, 26 prior to passing around the cooperating crimp roll 14. It will be understood by practitioners-in-the-art however, that opposed platens in an intermittent movement packaging machine may be utilized for joining the opposed webs together as discussed above.

After passing through nip 42, the joined together web 49 containing a plurality of incorporated flexible evacuated sealed packages in accordance with this invention, passes to a pair of rotary die cutters 46 for cutting out the individually formed packages from the opposed sealing webs. In doing so, the opposed sealed webs pass through guide rolls 44. The individual packages 54 drop into a guide station 55 on the top of conveyor 56. The belt of conveyor 56 passes over spaced apart rolls 58, 60 in a conventional manner. The conveyor 56 conveys the individual packages 54 to a receiving containing 62 at station 64 wherein filled containers 62 are removed so that the individual packages may be inspected.

As will be appreciated by practitioners-in-the-art, all of the rolls in the apparatus described are driven by motor 79 through conventional belts and reduction gearing in order to provide the proper sequential operation and rotational speeds of the various rolls for controlling the web passing through the apparatus. Moreover, control 66 controls through line 80 the dispensing container 34 and the quantity of materials passing through the lines 36 to make the appropriate quantities and timing of the materials 32 on the top of web 16.

As will be understood by practitioners-in-the-art, control 66 also controls through lines 76, 78, the required braking necessary for supply rolls 20, 22, respectively so that the webs 16, 18 are held in proper alignment for feeding to the cooperating crimp rolls 12, 14. Control 66, in turn, through lines 72, 74 controls the proper rotational speeds of the guide rolls 44 and the cooperating rotary die cutters 46. Control 66 through line 68 controls the speed of conveyor 56 for the proper takeoff of the final products 54 from station 55 to the waiting containers 62, and through line 77 the operation of corona station 84. If required, roll 26 may be in the form of a preheat roller in order to raise the temperature of web 18 prior to the entry of web 18 onto heated crimp roll 14 so that the thermoplastic material is in the proper form for properly joining and sealing to web 16 at nip 42.

A representative crimp roll 14 may have a plurality of pockets 40 along the longitudinal extend thereof with eight such pockets formed around the circumference thereof. Thus, eight packages may be formed in the cooperating nip 42 between crimp rolls 12, 14 at any one moment during the rotation of a roll 14. Under these circumstances, as will be appreicated by practitioners-in-the-art, a large quantity of flexible packages properly sealed may be produced simultaneously and continuously with the operation of the apparatus of the invention. Roll 14 may have a plurality of longitudinal passages in order to introduce heat into the cooperating rolls.

Figure 2:
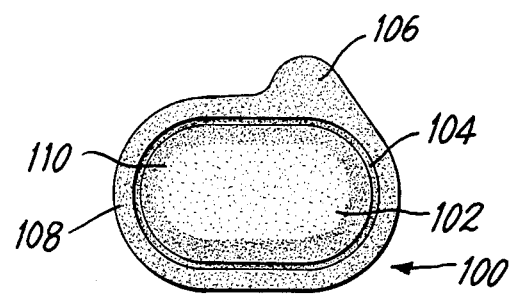
FIG. 2 is a plan view of one form of flexible package produced in accordance with the methods and apparatus of the invention.

FIG. 2 is representative of a flexible package produced in accordance with the methods and apparatus of the invention. As can be seen, the package 100 is configured in a generally oval shape with a tab 106 which is used as a guide tab for helping the user of a package 100 to grasp the peelable surface from the package in order to peel off and expose the adhesive coated membrane so that it may be exposed and applied to the skin of a patient for the slow dispensing of a medication from the package 100. The tab 106 is clearly shown outside the seal 104 formed around the center portion 102 containing the medication or other material contained in package 100. Outside the seal 104 is a border 108.

Figure 3:
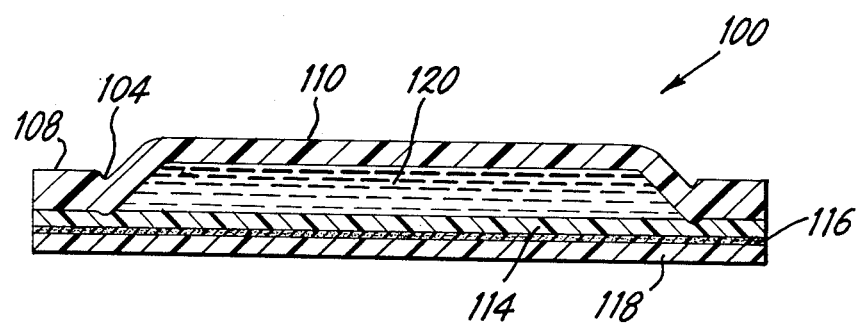
FIG. 3 is an enlarged sectional view of the package illustrated in FIG. 2 and showing the individual layers of material utilized to form the package.

Referring to FIG. 3, an enlarged longitudinal sectional view of a representative package produced in accordance with the methods and apparatus of the invention is shown. This package is the kind of package which may be utilized by the user to provide a uniform dispensing and dosing of a medication contained in the central portion 120 of the package through the skin of the user. Thus, as shown in FIG. 3, the package has a border 108 outside the sealed area 104 with a central container portion 120 of the package. The package includes a film backing 110 which provides appropriate "body" for the package. The film backing may be, for example, a film of a polyester laminated to ethylene vinyl acetate film.

The film 110 may be, for example, the web 18 as shown in FIG. 1. Forming web 16, for example, is a membrane film 114 which may be a transdermal material for allowing the passage of a medication contained in space 120 therethrough. Coated onto one surface of membrane 114 is an adhesive 116 to be described in more detail below. Finally, on top of adhesive 116 is a peelable layer 118 which is removed for use of the package if it is to be used as a transdermal dispensing package as described previously here. The peelable material may be, for example, a polyester. The adhesive layer may be, for example, a silicon based adhesive which would be appropriate for allowing the medication in container 120 to pass through membrane 114 to the skin once the adhesive layer 116 is exposed and the package adhered to the skin of the user.

As will be understood by practitioners-in-the-art, the various films will be selected depending upon the ultimate use of the flexible packages, in accordance herewith.

Accordingly, there is provided, as will be apparent from the foregoing, methods for producing a plurality of flexible packages on a continuous rapid basis. Moreover, the flexible packages are individually formed with a controlled quantity of material, sealed, to provide the individual self-contained packages. The methods herein are particularly appropriate for producing, automatically, transdermal medication packages so that a user may peel a film from the individual packages and adhere the packages to the skin for providing a regulated quantity of a medication through the skin to treat an individual. Large quantities of such packages may be produced much more rapidly than was the case previously in the same amount of time.

While the methods, and packages produced by the methods herein disclosed, form preferred embodiments of the invention, this invention is not limited to those specific methods and packages, and changes can be made therein without departing from the scope of the invention which is defined in the appended claims.

What is claimed is:

1. A process for the controlled simultaneous forming, filling, and sealing a plurality of flexible packages containing a material with a liquid component; comprising
    (a) supplying in a first supplying step a first web of material for forming a first side of the flexible packages to be formed;
    (b) supplying in a second supplying step a second web of material for forming a second side of the flexible package to be formed;
    (c) utilizing a pair of heated opposed surfaces positioned in cooperating engagement for receiving and joining said first and second webs from said first and second supplying steps in a flexible package forming area;
    (d) prior to said utilizing step, depositing a plurality of spaced apart quantitites of filling material for said packages on said first web from said first supplying step;
    (e) passing said web from said utilizing step to a cutting means;
    (f) cutting said web from said passing step into a plurality of filled flexible packages;
    the improvement characterized by the steps, of
    (g) prior to said utilizing step, exposing said first web of material to the effects of corona discharge;
    (h) said first web from said first supply roll is a laminate comprised of a membrane film layer, an adhesive film over one surface of said membrane film layer, and a peelable film on the side of said adhesive opposite said membrane film;
    (i) said membrane film allowing controlled passage of the contents of the package therethrough;
    (j) said membrane film being a silicone film having a chemically modified surface by exposure to corona discharge, and
    (k) said second web is a backing layer comprised of a laminate film of polyester laminated to a sealing film of polyvinyl acetate.

2. The process of claim 1, further characterized by
    (a) said utilizing step being carried out with a pair of crimp rolls, one of said crimp rolls having a plurality of pockets spaced apart circumferentially and longitudinally over the surface thereof;
    (b) said depositing step being carried out so that quantities of said material are deposited on said first web simultaneously in spaced apart fashion across the width of said first web and intermittently along the longitudinal extent of said first web; and
    (c) whereby said deposited quantities of said material on said first web mate with said pockets on said one crimp roll in said flexible package forming nip.

3. The package of claim 1, further characterized by
    (a) the contents of said package is a cream medication for continuous dispensing through said membrane and adhesive layers to the user's skin.

4. The package of claim 1, further characterized by
    (a) said membrane film is polydimethylsiloxane.

* * * * *